United States Patent [19]

Kuntschik et al.

[11] 3,960,955

[45] June 1, 1976

[54] PURIFICATION PROCESS

[75] Inventors: Lawrence F. Kuntschik, Nederland; Orville W. Rigdon, Groves, both of Tex.

[73] Assignee: Texaco Inc., New York, N.Y.

[22] Filed: Nov. 15, 1974

[21] Appl. No.: 524,109

[52] U.S. Cl. .................. 260/566 A; 260/96.5 R
[51] Int. Cl.² ................................. C07C 131/00
[58] Field of Search ............. 260/96.5 R, 96.5 U, 260/96.5 T, 566 A

[56] References Cited
UNITED STATES PATENTS

| | | | |
|---|---|---|---|
| 2,569,985 | 10/1951 | Fetterly | 260/96.5 |
| 2,681,334 | 6/1954 | Gorin | 260/96.5 |
| 3,316,236 | 4/1967 | Starks et al. | 260/96.5 |
| 3,534,097 | 10/1970 | Williams | 260/96.5 |
| 3,717,623 | 2/1973 | Ruyle | 260/96.5 |

*Primary Examiner*—Delbert E. Gantz
*Assistant Examiner*—C. E. Spresser
*Attorney, Agent, or Firm*—T. H. Whaley; C. G. Ries; Bernard Marlowe

[57] ABSTRACT

This invention concerns a process for purifying crude oximes, particularly crude n-paraffinone oximes containing carbonyl and/or chlorine contaminants, consisting essentially of treating said crude oximes with urea or thiourea, in the presence of water and lower alkanol, heating to decompose thermally unstable contaminants, filtering off the insoluble urea (or thiourea) carbonyl complexes formed, leaving a purified oxime which can be further purified by conventional purification methods such as vacuum distillation.

8 Claims, No Drawings

PURIFICATION PROCESS

This process concerns a method for purifying crude oximes containing substantial quantities of carbonyl-type and/or chlorine contaminants by treatment of a urea-type reagent in the presence of a water-inert solvent mixture to form a carbonyl-urea complex relatively insoluble in the reaction media and using the insolubility of said complex to separate the carbonyl-type complex from the soluble oxime and recovering the oxime in a purified and/or concentrated form by extraction using an appropriate solvent system or by any other conventional purification technique.

More particularly, this invention relates to a process wherein a crude oxime product containing carbonyl-type and chlorine impurities derived from a photolytic catalyzed nitrosation of $C_{10}$–$C_{15}$ mixture of n-paraffins, preferably using nitrosyl chloride and hydrogen chloride, is freed of carbonyl-type and chlorine impurities by heating the crude oxime reaction medium consisting essentially of oxime, ketones and organic chlorides with urea, water and/or lower alkanol at elevated temperatures until the chloride impurities are converted to ketones and urea-ketone complexes are formed, cooling and filtering off the insoluble urea-ketone complex from the residual oxime-rich filtrate, concentrating the purified oxime by solvent extraction or equivalent methods, optionally followed by further purification techniques such as extraction and/or distillation under low pressures.

BACKGROUND OF THE INVENTION

Oximes are useful as organic intermediates and for various other applications. For example, they undergo the Beckmann rearrangement, can be alkoxylated and hydrogenated, and are useful as lubrication additives and anti-icing additives. Some oximes can be converted to synthetic fibers (i.e. cyclohexanone oxime can be converted into caprolactam, an intermediate for the commercial preparation of Nylon 6).

Paraffinone oximes have been prepared by the base catalyzed reaction of ketones with hydroxylamine salts and more recently by the photolytic nitrosation of normal paraffins. Both of these synthetic methods can produce a crude product which contains substantial quantities of contaminants boiling close to or overlapping the boiling points with the oxime product. Most of these impurities encountered in both processes are aldehydes or ketones (which are referred to generically as carbonyl-type impurities), while in the photolytic process gem-nitrosochlorides and gem-nitrosochloride condensation products can also cause separation problems. In any event, conventional distillation under high vacuum of the crude oxime obtained through photolytic nitrosation fails to produce high purity (i.e., 95 percent or higher) products free from ketone impurities. Examples 1 and 2 provide evidence of this anomaly.

In view of the separation difficulties presented by these impurities, there is a need for a purification procedure directed to the purification of paraffinone oximes containing substantial quantities of carbonyl-type and organic chlorine impurities. Particularly useful would be a simple treatment whichh would utilize as starting material a crude oxime product derived from the photolytic nitrosation of n-paraffins such as disclosed in U.S. Pat. No. 3,578,575, and which contains substantial quantities of carbonyl-type and/or organic chlorine impurities. Desirably, the purification procedure would utilize the 95 percent and lower oxime content product of the above application and convert it to a product of 98 percent and higher oxime content. Ideally, the novel process would be relatively inexpensive, would require no particular expertise and would utilize commercially available equipment.

BRIEF DESCRIPTION OF THE INVENTION

In practice, an oxime product, however derived, contaminated with substantial quantities of carbonyl-type and/or organic chlorine impurities is treated at elevated temperatures, in an aqueous-inert, solvent medium with urea-type reagent. Sufficient urea-type reagent is used to convert all of the carbonyl-type impurities present to a urea-type complex insoluble in the reaction medium. The heating with stirring is continued until the organic chloride impurities are decomposed. Then the reaction medium is cooled and the urea-type carbonyl complex precipitates out. At this time the insoluble urea-type carbonyl complex is usually removed from the oxime for further use.

In the favored practice, a paraffinone oxime product containing from 5 to 30 or more carbon atoms, having an oxime content of 95% by weight or less, and containing a substantial quantity of carbonyl-type and organic chloride impurities, is treated at about 25° to 200°C, in the presence of a water-lower alkanol mixture with 10 to 100% by weight of urea (based upon the amount of the crude oximes to be purified) to form a reaction mixture. The heating of said mixture is continued until the organic chloride impurities are decomposed, the mixture is then cooled to facilitate precipitation of the urea-carbonyl complex which is separated from the purified oxime for further use and/or purification.

In the preferred practice, a crude oxime product derived from the photolytic nitrosation of n-paraffins with nitrosyl chloride and hydrogen chloride containing from 10 to 15 carbon atoms, said product having an oxime content of 95 percent or less, and containing up to 10% by weight or more of ketones and organic chloride impurities, is a. mixed with from about 10 to 100% by weight urea in the presence of 1 to 20% by weight water and 2 to 50% by weight methanol, then heated between about 25° to 125°C until the thermally unstable chlorides are decomposed and converted to ketones;

b. cooled below 25°C to facilitate precipitation of all the ketones to the insoluble urea-ketone complex;

c. filtered to remove the urea-ketone complex, leaving the purified oxime soluble in the filtrate, and d. extracted or distilled to separate the purified oxime contained therein.

DETAILED DESCRIPTION OF THE INVENTION

In order to aid in the understanding of the inventive process, the following additional disclosure is submitted.

A. Paraffinone Oxime Product — Any oxime, particularly, paraffinone oxime products containing at least 5 carbon atoms up to 30 or more carbon atoms, can be utilized as charge stock as long as it contains substantial quantities of carbonyl-type and/or organic chlorine impurities. The favored oximes are the linear and cyclic crude oximes such as the hexanone oximes, the cyclohexanone oximes, the heptanone oximes, the octanone oximes, the nonanone oximes, the decanone oximes, the undecanone oximes, the dodecanone oximes, their higher homologues and/or mixtures thereof. The preferred oximes are crude cyclohexanone oximes and the paraffinone oximes containing 10 to 15 carbon atoms and having 95% or less oxime content. They can be in the form of the relatively dry, crude single oxime product, free from inert solvent, or as mixtures of the oximes having 10 to 15 carbon atoms, either relatively free from solvent or containing up to 25% by weight of inert solvent. The $C_{10}$ to $C_{15}$ group of oximes, whether solvent-free or not, are preferred because they are available in large quantities from the nitrosation of the corresponding paraffins as described in U.S. Pat. No. 3,578,575.

B. Urea-Type Complexing Reagent. The "urea-type" reagent is selected from the group consisting of urea, thiourea and mixtures thereof. These reagents are employed in sufficient quantities to complex at least all of the ketones contained in the crude oxime including the ketones obtained through decomposing the chloride impurities originally present in the oxime. These complexing reagents are ordinarily employed in stoichiometric excess (based upon ketone present and ketone to be formed from chloride impurities in the crude oxime). In practice where from about 5 to 10% ketone is present in the oxime from 10 to 100% by weight of urea based on the oxime charge is employed. If thiourea is employed a proportionately higher range is required.

C. Water — The presence of water during the formation of the urea-carbonyl-type complex is critical for the satisfactory removal of ketones (or aldehydes) from the crude oximes. Satisfactory results have been obtained when from about 1 to 20% by weight of water (based upon the quantity of oximes) is present with the preferred results consistently being noted when about 4 to 15% by weight of water is present during complex formation. Further, the presence of water leads to the conversion (during the heating) of nitrosochlorides and related compounds present to ketones which subsequently complex with the urea-type reagent. Finally, based upon the results shown in Examples 6 through 12, the satisfactory removal of ketones (or aldehydes) from the crude oxime can only be accomplished in the presence of a water-alkanol solvent system, particularly when the mole ratio of water varies from 0.1 to 2.0 moles of water per mole of alkanol present.

D. Cosolvent with Water — As indicated supra water and at least one inert, water-miscible solvent must be employed for effective removal of carbonyl-type impurities from the crude oxime through separation of the urea-type complex which is insoluble in the reaction media. While alkanols containing 1 to 5 carbon atoms are useful, and methanol is preferred, other inert solvents can be employed. These are illustrated by the following solvents, among others: acetone, methyl ethyl ketone, methyl acetate and the like.

E. Solvents employed to wash Urea-type Carbonyl Complexes — In order to minimize the loss of oxime entrained in the insoluble Urea complexes, wash solvents having limited urea or thiourea solubility, i.e. less than 0.1% by weight of urea in the solvent can be used.

F. Reaction Conditions:

1. Temperature — The reaction temperatures required for the inventive process are relatively flexible, ranging from about 25° to 200°C. In view of the fact that the best results have been obtained between about 25° to 125°C, these temperatures represent the preferred range.

2. Pressure — Ordinarily atmospheric or near atmospheric pressures are employed. Since no apparent advantage results from the use of super or sub-atmospheric pressures and these extremes of pressures are more costly to maintain, atmospheric pressures are preferred.

3. Reaction Time — The reaction time varies according to the reaction temperature and concentration of charge used, as well as the size of the batch being treated, and for these reasons cannot be defined precisely. However, under most conditions the reaction will be completed within 0.1 to 12 hours of treatment with longer times not being harmful. Under the more usual reaction conditions the reaction will be complete within about 1 to 2 hours.

4. Separation of Solid Materials — The separation of the precipitate of carbonyl-urea complex and the exclusion of entrained oxime is assured by washing the complex with solvents having limited urea solubility. These include among others, alkanes from pentane to decane and their mixtures, cycloalkanes, cyclohexanes etc., cold alkanols containing from 1 to 5 carbon atoms and their mixtures as well as ketones containing 3 to 10 carbon atoms and mixtures.

5. Mole Ratio of Urea Type Material to Crude Oxime — Fairly good results have been obtained with urea/oxime mole ratios of 0.3 to 3.0 of urea for each mole of crude oxime to be purified. However, consistently good results have been obtained with urea to oxime mole ratios ranging from 0.5 to 2.0 and these represent the preferred ratios.

6. Mole Ratio of Urea to Ketone in Oxime — While a mole ratio of 5 to 50 moles of urea type complexing agent per mole of the ketone impurities known to be present in the crude oxime to be purified is satisfactory, the preferred weight ratio is from about 10 to 25 moles of urea per gram of ketone present in the oxime. The narrower mole ratio is preferred because it produces a consistently good yield of purified oxime free essentially from carbonyl impurities particularly of ketones.

G. Process Conditions:

As described supra, the gist of this invention is the discovery that the oxime content of crude oximes can be substantially increased with a corresponding decrease in the proportion of contaminants of the carbonyl type (essentially ketones) as well as those referred to as organic chloride impurities by urea or thiourea complex formation in a water-based solvent system. In these systems oximes do not appear to form urea* (or thiourea) complexes whereas insoluble urea-type carbonyl complexes are readily formed. This is particularly useful in crude oximes containing 90 to 95% of oximes and 5 to 10% by weight of said carbonyl-type (largely ketones) impurities and the aforementioned chlorine containing compounds constituting the remainder of the impurities. Crude oximes of this type are derived from photolytic nitrosation sources, particularly from processes derived from the photolytic nitrosation of the corresponding n-paraffins. Peculiarly enough, unless the photolytically derived oximes are initially treated with a strong base prior to distillation, even molecular distillation fails to maintain the initial reduction in carbonyl-type plus organic chloride impurities. (See U.S. Pat. No. 3,764,622.) Further, the patented process has the disadvantage of converting the ketone impurities to heavy residuum condensates which can only be discarded whereas the instant process permits the ketones to readily be recovered and be sold as chemical intermediates. Moreover, the urea-ketone complexes form selectively even when in the presence of large excesses of mixtures of $C_{10}$ to $C_{15}$ paraffinone oximes.

\* The closest known prior art is Industrial and Engineering Chemistry, Vol.47, pages 216–222 which discloses urea-ketone among many other complexes but fails to teach the use of these complexes as an oxime purification technique.

In the most preferred process, the steps for purifying the crude oxime consist essentially of:

1. Admixing a crude oxime mixture of n-paraffinone oximes having 10 to 15 carbon atoms containing 90 to 95% oxime and 5 to 10% by weight ketones and from about 0% to 5% of organic chlorides (based upon initial oxime content) with from 15 to 70% by weight of urea in the presence of 4% to 15% water and from 5 to 30% by weight of lower alkanols, for 0.5 to 5 hours at temperatures ranging from about 85° to 125°C to decompose the aforementioned organic chloride impurities to ketones forming a mixture of the soluble oxime and insoluble urea-ketone complex, 2. Cooling the mixture of said soluble and insoluble urea complexes to about −10° to +10°C, separating the insoluble urea-ketone complex from the soluble oxime by filtration, centrifugation and the like.

3. Washing the insoluble urea-ketone complex with solvent in which urea has a limited solubility and combining the wash liquid with the soluble oxime-rich filtrate, and 4. Subjecting the solution of oxime-containing filtrate plus washings, to dilution with about 10 to 100% by volume with water, and extracting said water-diluted oxime-rich solution with a solvent such as dialkyl ethers and stripping off the solvent from the purified oxime to recover the purified oxime.

H. Distillation at High Vacuum — Optionally, the purified oxime recovered by stripping off solvents can be further purified especially in regard to color removal by distillation under high vacuum. By High Vacuum Distillation is meant distillations carried on at less than 10 mm of mercury, preferably under 1 mm of mercury. While no particular mode of vacuum distillation is required, especially good results have been obtained using molecular distillation techniques and for this reason these techniques are favored. Molecular distillations as used herein refer to those distillation means where the vapor path of the molecules being distilled is unobstructed and the condenser in the apparatus is separated from the evaporation by a distance less than the mean free path of the evaporating, emerging molecules. While molecular distillation techniques are favored, as is frequently the case where a species selected from a broad class is employed, a more specific technique or process within the broad class is preferred for one reason or another. In the instant case, distillation within a molecular pot still is preferred since it preserves the low contaminant level of the treated oxime substantially unchanged. These types of distillations can be carried out in a variety of apparatus at vacuums ranging from 0.001 to 0.0001 mm of mercury. Two types of commercially available molecular stills which are widely used employ either centrifugal or continuous (or falling) film techniques. Illustrative stills are described in Chapter 17, pages 29–32, of the *Chemical Engineering Handbook* by Perry, Chilton and Kirkpatrick, 4th Edition, published by McGraw Hill Inc., New York, N.Y., among other publications.

Having described the inventive process in general terms, the following examples and embodiments are submitted to supply more detailed illustrations of its workings.

Embodiment A — Preparation of a Crude Mixed $C_{10}$–$C_{13}$ Paraffinone Oxime Product Containing Substantial Quantities of Carbonyl-Type Impurities:

A 22.981 kg. portion of mixed $C_{10}$–$C_{13}$ n-paraffins is charged to a photoreactor equipped with heating and cooling means and a means of directing a light source which excludes wave lengths below 200 millimicrons. The paraffin mixture is reacted with an excess of gaseous nitrosyl chloride at 60°F in the presence of gaseous hydrogen chloride at flow rates of 1.64 grams per minute and 0.95 grams per minute, respectively. After separation of the crude oxime-acid salt, the acid is neutralized with aqueous ammonia and the crude $C_{10}$–$C_{13}$ oxime mixture is separated. The molar selectivity to crude oximes is 87.4% with an overall recovery of 90.7% by weight oxime. The crude oxime product contains about 4% by weight of $C_{10}$–$C_{13}$ ketones.

EXAMPLE 1

Attempted Purification of Neutralized Crude $C_{10}$–$C_{13}$ N-paraffinone Oxime Mixture Using Conventional Distillation Under Moderate Vacuum An 800-gram crude mixture of $C_{10}$–$C_{13}$ n-paraffinone oxime prepared as in Embodiment A and containing 4.3% by weight of ketones and 0.41% by weight chlorine is batch vacuum fractionated at 0.4 to 0.6 mm of mercury on an 18 inch Hempel column packed with ¼ inch protruded stainless steel packing in the presence of 100.0 grams of 700°F hydrocarbon chaser. The following summarizes the results:

| Fraction No. | Boiling Point, °C | Pressure mm Hg | Wt., grams | % by weight of Ketones in Fraction |
|---|---|---|---|---|
| 1 | 100 | 0.5 | 6.0 | 50 |
| 2 | 110 | 0.6 | 74.0 | 19 |
| 3 | 108 | 0.4 | 164.1 | 13 |
| 4 | 108 | 0.4 | 204.3 | 9 |
| 5 | 112 | 0.4 | 101.2 | 13 |
| 6 | 120 | 0.5 | 37.0 | 19.5 |
| 7 | 130 | 0.6 | 58.2 | 30 |

As the increases in ketones (>175 by weight increase) indicates, conventional vacuum distillation without prior treatment with urea-type reagents to remove ketone contaminants actually worsens the purity of oxime product. This distillate product exhibits an undesirable hazy appearance.

EXAMPLE 2

Attempted Purification of Crude $C_{10}$–$C_{13}$ N-paraffinone Oxime Mixture Using Continuous Thin Film Distillation (Distillation Under High Vacuum) Without a Preceding Purification with Urea A 90-gram portion of crude $C_{10}$–$C_{13}$ paraffinone oxime prepared as in Embodiment A and containing 3.6% by weight of ketones and 1.15% by weight of chlorine, is charged to a 2 inch Rodney Hunt Vacu-Film Processor, sold by Rodney Hunt Machine Company (currently sold by Arthur F. Smith Co.) and heated to 100° to 105°C at 0.3 mm Hg pressure. A light colored oxime distillate (67.0 grams) containing 2.6% by weight of ketones and 0.93% by weight of chlorine is obtained. The product exhibits an undesirable hazy appearance.

This example demonstrates that without the novel preceding treatment with urea (or thiourea) to remove ketones, continuous thin film distillation is not a singly effective means of substantially removing carbonyl-type and organic chlorine impurities from the crude oxime.

EXAMPLE 3

Failure of Urea to Remove Impurities Contained in Crude Mixtures of $C_{10}$–$C_{13}$ Paraffinone Oximes (Obtained Through Photolytic Nitrosation of N-paraffins) Unless Water Is Present During Complexation A 50-gram mixture of $C_{10}$–$C_{13}$ paraffinone oximes prepared as in Embodiment A, containing approximately 5% by weight of ketones and 1.5% by weight of chlorine is mixed with 500 ml of mixed heptanes, 20 ml of methanol and 80 grams of urea in a reaction vessel and heated to 22°C for 1 hour. After vacuum filtration of the precipitated crystal complexes the crystals are washed with mixed heptanes (50 ml) and dissolved in 200 ml of deionized water. The aqueous solution yields only a trace of ketone impuriity after extracting twice with 100 ml of diethyl ether, pooling the ether extracts and evaporating off the ether solvent. The filtrate and washes, presumably oxime free from ketones, are pooled and washed with 200 ml of deionized water, dried and stripped under vacuum to yield 41 grams of recovered oxime. Upon analysis, however, the ketone content is not appreciably less than the initial 5% by weight concentration. This, when taken together with the following examples, is indicative of the fact that water should be present for effective formation of a urea-ketone complex that will remove ketones from the crude oxime. The substitution of thiourea for urea upon a mole by mole basis is also ineffectual for the removal of ketones from the crude oxime.

EXAMPLE 4

Failure of Urea to Remove Ketone Impurities Contained in Crude Oximes in the Presence of Lower Alkanols but in the Absence of Water During Complex Formation A 120 gram portion of urea and 500 ml of absolute methanol are heated to reflux and 20 grams of crude n-$C_{10}$–$C_{13}$ oxime mixture (containing 5% by weight of ketone and 1.5% by weight of chlorine) and 100 ml of mixed heptanes are charged to the agitated refluxing charge. After 2 hours the reaction is stopped, and reaction mixture is cooled to about 5°C and the crystal complex which forms is vacuum filtered. The crystals are washed twice with 50 ml of mixed heptanes and are then dissolved in 200 ml of deionized water. The resultant solution is extracted twice with 100 ml portions of diethyl ether. The ether is evaporated under vacuum to yield only 0.02 grams of ketone. The filtrate (and washes) are washed with 200 ml of deionized water, dried and stripped of solvent to yield 16 grams of recovered oximes. Analysis of the oxime product shows that essentially no ketones are separated from the oxime by this procedure.

The substitution of ethanol for methanol on a mole for mole basis gives the same poor results.

EXAMPLE 5

Failure of Urea to Remove Ketone Impurities Contained in Crude Oxime in the Presence of Water but in the Absence of Lower Alkanol During Complex Formation A 50 gram portion of a crude n-$C_{10}$–$C_{13}$ oxime mixture (containing 4.3% by weight of ketones and 1.12% by weight of chlorine) and 100 grams of distilled water are refluxed for 3 hours. After cooling, the mixture is extracted twice with 100 ml of cyclohexane and the pooled cyclohexane extract is stripped in vacuum to remove the cyclohexane. A 31-gram portion of oxime obtained from the cyclohexane extraction (containing 7.2% by weight of ketone) is mixed with 25 grams of urea and 25 ml of absolute methanol and the mixture is kept for 30 minutes at 22°C. After cooling to about 5°C in an ice bath the crystals of urea complex are vacuum filtered. The crystals are then dissolved in 50 ml of water and the aqueous solution is extracted twice with 20 ml portions of diethyl ether. From the pooled ether extracts, a one-gram portion of liquid containing 40% by weight of ketones is recovered by evaporation of the ether. The oxime-rich filtrate from the crystal filtration is diluted with 50 ml of water and extracted twice with 100 ml portions of diethyl ether. The pooled ether extracts are stripped off yielding 28 grams of oxime containing 4.9% by weight ketone. Not only are poor yields of oxime obtained but the diminution of oxime actually increases ketone content (from 4.3% by weight to 4.9% by weight) over the proportion of ketone present prior to treatment.

EXAMPLES 6 THROUGH 12

In the following examples 187 gram portions of crude oximes produced as described in Embodiment A containing 4.3% by weight of ketones are contacted with quantities of urea ranging from 30 grams to 120 grams in the presence of both methanol (ranging from 0 [Example 11] to 50 grams), and water (varying) from 9 to 20 grams. The process consists essentially of:

a. Heating the reaction mixture of crude oxime(s), methanol (except in Example 11) and water to reflux while stirring for an hour to decompose any organic chlorine compounds present and to form the urea-ketone complexes, b. Cooling the reaction mixture to between about −10° to +10°C until the insolubility of the precipitate of urea-ketones is optimized, c. Filtering off the crystals using from 10 to 50 ml of methanol kept between about −10° to +10°C as a wash, d. Diluting the oxime-rich filtrate and methanol washes with 100 ml of water and extracting twice with 50 to 100 ml portions of diethyl ether to remove the oximes present in the filtrate and wash solutions, and e. Stripping off the ether to produce the purified oxime.

The following Table summarizes the data obtained.

TABLE

| CHARGE COMPOSITION | EXAMPLES | | | | | | |
|---|---|---|---|---|---|---|---|
| | 6 | 7 | 8 | 9 | 10 | 11 | 12 |
| $C_{10}$-$C_{13}$ OXIMES[a] | ———————— PREPARED AS IN EXAMPLE 1 ———————— | | | | | | |

TABLE-continued

| CHARGE COMPOSITION | EXAMPLES | | | | | | |
|---|---|---|---|---|---|---|---|
| | 6 | 7 | 8 | 9 | 10 | 11 | 12 |
| wt., grams | 187 | 187 | 187 | 187 | 187 | 187 | 187 |
| wt. % ketones | 4.3 | 4.3 | 4.3 | 4.3 | 4.3 | 4.3 | 4.3 |
| Urea wt. grams | 120 | 60 | 60 | 120 | 30 | 30 | 60 |
| Methanol Wt. grams | 50 | 32 | 32 | 32 | 16 | — | 16 |
| Water wt. grams | 20 | 18 | 9 | 18 | 9 | 9 | 18 |
| Urea/oxime, mole ratio | 2.0:1 | 1.0:1 | 1.0:1 | 2.0:1 | 0.5:1 | 0.5:1 | 1.0:1 |
| Urea/ketone, mole ratio | 42.5:1 | 21.25:1 | 21.25:1 | 42.5:1 | 10.6:1 | 10.6:1 | 21.25:1 |
| Urea/oxime/water, mole ratio | 1.8:1 | 1.0:1 | 2.0:1 | 2.0:1 | 1.0:1 | 1.0:1 | 1.0:1 |
| moles water | 1.11 | 1.0 | 0.5 | 1.0 | 0.5 | 0.5 | 1.0 |
| Treatment Temperature | 190 | 190 | 190 | 190 | 190 | 190 | 190 |
| Time (on Temp.) Hrs. | 1.0 | 1.0 | 1.0 | 1.0 | 1.0 | 1.0 | 2.0 |
| Recovery Stripped Filtrate | | | | | | | |
| Wt. grams | 132.4 | 133.6 | 108.9 | 161.2 | 161.4 | 174.8 (b) | 162.7 (b) |
| Wt. % ketones | 0.75 | 1.8 | 1.4 | 1.6 | 3.1 | 4.8 | 2.0 |
| Product from Urea Crystals | | | | | | | |
| Wt. grams | 16.5 | 38.8 | 44.6 | 19.3 | 15.0 | 3.2 | 14.3 |
| Wt. % ketones | 40 | 10.8 | 10.5 | 40 | 40 | 9.3 | 40 |

(a) Oxime contained 1.12 wt. % of chlorine
(b) Urea crystals were washed with petroleum ether prior to decomposition Embodiment B — Preparation of a Specific Oxime-Containing Substantial Quantities of Carbonyl-Type Impurities:

Using the general procedure described in Sedgwick, Organic Chemistry of Nitrogen, pages 169-175 (1937 Edition), 1.2 moles of 6-undecanone is reacted with an alcohol solution of 1 mole of hydroxylamine at room temperature to produce 0.8 moles of 6-undecanone oxime,

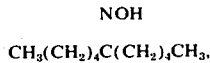

$$CH_3(CH_2)_4C(CH_2)_4CH_3,$$

with NOH above, contaminated with 3.5% 6-undecanone.

EXAMPLE 13

Purification of a Specific Paraffinone Oxime Containing Substantial Quantities of Carbonyltype Impurities The 0.8 mole portion of 6-undecanone oxime prepared in Embodiment B is thoroughly mixed with 50 grams of absolute methanol, 20 ml of water and 120 grams of urea to form a reaction mixture. The reaction mixture is heated to reflux for two hours then cooled to about 0°C at which point the precipitate of urea-ketone complex is filtered off and washed with 20 ml of chilled methanol to remove entrained oxime. At this time the filtrate and methanol are diluted with 100 ml of water, extracted twice with diethyl ether and vacuum stripped of solvent producing a purified 6-undecanone oxime containing about 0.7% by weight ketones.

This example demonstrates:

1. That the claimed process is applicable to purify specific oximes rather than only to mixtures of oximes, and 2. That the process is useful to purify crude oxime substrates derived from other than photolytic nitrosation procedures.

As the several examples have indicated, the novel oxime purification process is both surprising and advantageous over the known prior art. For instance, while it is well known that a large group of compounds including ketones form urea or thiourea complexes it was not known that crude oximes containing ketones and organic chlorine impurities could be purified by preparing urea (or thiourea) inclusion complexes of said ketones contained in said crude oximes. It was also quite unexpected to find that a useful oxime purification process not only required formation of the urea-ketone complexes but that few or none of the ketones contained in the crude oximes can be removed as the urea-ketone complex unless from about 4 to 15% by weight of water is present with the lower alkanol during the formation of said urea-alkanol complex. See Examples 1 to 5 for documentation of this. In addition, the claimed process offers the ancillary advantage of decomposing organic chlorine compounds during the heating (usually refluxing) step that accompanies urea-ketone complexation. Further, inasmuch as the chlorine-containing compounds are converted to ketones, the addition of urea complexes the converted ketones produced as well as the ketones originally present in the crude oxime. In contrast to conventional oxime purification, this process is advantageous in that it permits the recovery of the ketones removed from the oxime in a marketable form. Other advantages are the use of commonplace process techniques without the need for elevated reaction temperatures and pressures, as well as the low costs of the urea or thiourea which can be readily purified for further use. Finally, while water is essential during complex formation the lower alkanols, particularly methanol or ethanol can be used as cosolvent, and the purified oxime may further be purified by well known techniques such as molecular distillation and/or chromatographic separation techniques without departing from the inventive concept. The metes and bounds of this invention are best determined by the claims which follow, read in conjunction with the specification.

What is claimed is:

1. A process for purifying crude paraffinone oximes containing from 5 to 30 carbon atoms, from impurities consisting essentially of from about 0 to 20% by weight of carbonyl compounds and from about 0 to 4% by weight of organic chlorine impurities, said precentage of impurities based upon the weight of oxime, by:

a. forming a reaction mixture by mixing each part by weight of paraffinone oxime to be purified with from about 0.01 to 0.2 parts by weight of water, from about 0.02 to 0.5 parts by weight of a lower alkanol containing from 1 to 5 carbon atoms, and with from about 0.1 to 1 parts by weight of a complexing reagent selected from the group consisting of urea and thiourea, the urea or thiourea being added in the presence of water, b. heating said reaction mixture between about 25° to 200°C until the organic chlorine impurities are decomposed and an insoluble carbonyl complex is formed, c. cooling said reaction mixture to between about −10° and +10°C, and d. removing the insoluble carbonyl complex from the purified oxime contained therein.

2. The process of claim 1 wherein the crude paraffinone oximes are in the form of a mixture of 5 to 30 carbon atoms and the urea-type reagent is urea.

3. The process of claim 1 wherein the crude paraffinone oximes are in the form of a specific compound.

4. A process for purifying crude paraffinone oximes containing 10 to 15 carbon atoms, said oximes being derived from the photolytic nitrosation of n-paraffins containing from 10 to 15 carbon atoms, said crude oximes containing from about 0% to 20% of carbonyl and nitrosochloride impurities, by:

a. forming a reaction mixture by mixing each part by weight of crude paraffinone oxime to be purified with from about 0.1 to 1 parts by weight of urea complexing reagent selected from the group consisting of urea and thiourea, in the presence of from about 0.02 to 0.20 parts of water and from about 0.02 to 0.5 parts by weight of alkanol containing from 1 to 5 carbon atoms, b. heating said reaction mixture to reflux for about 0.5 to 5 hours to convert the nitrosochloride impurities to ketones and to form an insoluble ketone complex, c. cooling said reaction mixture between about −10° and +10°C for at least 0.2 hours, d. separating said insoluble complex from the cooled reaction mixture, and e. isolating the purified oxime contained therein.

5. The process of claim 4 wherein the lower alkanol is methanol, the carbonyl impurities are ketones and the complexing reagent is urea.

6. The process of claim 4 wherein the cooled insoluble complex is washed with methanol kept at least about +10°C, the washings are added to the cooled reaction mixture extracted at least twice with dialkyl ether and the purified oxime isolated by removing the solvents under vacuum.

7. The process of claim 4 wherein the crude paraffinone oxime is a specific paraffinone oxime.

8. The process of claim 4 wherein the crude paraffinone oximes are in the form of a mixture.

* * * * *